US009824870B1

(12) United States Patent
Straume et al.

(10) Patent No.: US 9,824,870 B1
(45) Date of Patent: Nov. 21, 2017

(54) PORTABLE MEDICAL DIAGNOSIS INSTRUMENT

(71) Applicant: The United States of America as represented by the Administrator of the National Aeronautics & Space Administration (NASA), Washington, DC (US)

(72) Inventors: Tore Straume, Rocklin, CA (US); David J. Loftus, Palo Alto, CA (US); Jing Li, San Jose, CA (US); Cristina E. Davis, Davis, CA (US); Anup K. Singh, Livermore, CA (US); Matthew A. Coleman, Livermore, CA (US)

(73) Assignee: The United States of America as Represented by the Administrator of NASA, Washington, DC (US)

( * ) Notice: Subject to any disclaimer, the term of this patent is extended or adjusted under 35 U.S.C. 154(b) by 0 days.

(21) Appl. No.: 14/700,019

(22) Filed: Apr. 29, 2015

Related U.S. Application Data

(60) Provisional application No. 61/985,953, filed on Apr. 29, 2014.

(51) Int. Cl.
*H01J 49/02* (2006.01)
*G01N 33/487* (2006.01)
(Continued)

(52) U.S. Cl.
CPC ........ *H01J 49/0031* (2013.01); *G01N 27/622* (2013.01); *G01N 33/483* (2013.01)

(58) Field of Classification Search
CPC .... G01N 27/622; G01N 33/483; G01N 33/48; G01N 33/487; G01N 33/493; G01N 33/497; G01N 33/50
See application file for complete search history.

(56) References Cited

U.S. PATENT DOCUMENTS 7,057,168 B2 6/2006 Miller et al.
7,355,170 B2 4/2008 Miller et al.
(Continued)

OTHER PUBLICATIONS

Straume, et al., Meeting Report, NASA Radiation Biomarker Workshop, Sep. 27-28, 2007, 393-405, 170, Radiation Research, Radiation Research Society.
(Continued)

*Primary Examiner* — Paul Hyun
(74) *Attorney, Agent, or Firm* — John F. Schipper; Robert M. Padilla; Mark P. Dvorscak

(57) ABSTRACT

A system that integrates several technologies into a single, portable medical diagnostic apparatus for analyzing a sample body fluid (liquid and/or gas): (1) a mechanism to capture airborne microdroplets and to separate the body fluid into a first fluid component (primarily gas) and a second fluid component (primarily liquid); (2) a volatilizer to convert a portion of the second fluid component into a third fluid component that is primarily a gas; (3) a functionalized nanostructure (NS) array configured to receive, identify, and estimate concentration of at least one constituent in the first and/or third fluid components; (4) a miniaturized differential mobility spectrometer (DMS) module; and (5) a biomarker sensor, to detect volatile and non-volatile molecules in a sample fluid, which may contain one or more components of blood, breath, perspiration, saliva, and urine.

13 Claims, 6 Drawing Sheets

(51) Int. Cl.
*G01N 33/497* (2006.01)
*G01N 33/50* (2006.01)
*H01J 49/00* (2006.01)
*G01N 27/62* (2006.01)
*G01N 33/483* (2006.01)

(56) References Cited

U.S. PATENT DOCUMENTS

| | | | |
|---|---|---|---|
| 7,388,195 | B2 | 6/2008 | Zapata et al. |
| 7,470,898 | B2 | 12/2008 | Merrick et al. |
| 7,576,319 | B2 | 8/2009 | Miller et al. |
| 7,968,842 | B2 | 6/2011 | Zapata et al. |
| 2005/0051719 | A1* | 3/2005 | Miller .................. G01N 27/622 250/287 |
| 2006/0163471 | A1* | 7/2006 | Zapata ................. G01N 27/624 250/288 |
| 2011/0098591 | A1* | 4/2011 | Haick .................... B82Y 15/00 600/532 |

OTHER PUBLICATIONS

Bohrer, et al., Biomolecule Analysis by Ion Mobility Spectrometry, Annual Review of Analytical Chemistry, Feb. 27, 2008, Indiana University, Bloomington, Indiana.

Ramakrishnana, et al., Extended Abstracts Predicting Individual Radiation Sensitivity: Current and Evolving Technologies, Radiation Research, Mar. 17-18, 2008, 666-675, 170, Radiation Research Society.

Zhao, et al., Miniature Differential Mobility Spectrometry (DMS) Advances towards Portable Autonomous Health Dianostic Systems, Wearable and Autonomous Devices and Systems for Smart Environment, Lecture Notes in Electrical Engineering, 2010, 55-73, 75, Springer-Verlag Berlin Heidelberg.

Bardaweel, et al., Microscale Surface Energy Properties for Enhanced Surface Condensation and Sampling of Exhaled Breath Metabolites, Proceeds of the Solid-State Sensors, Actuators, and Microsystems Workshop, Jun. 3-7, 2012, 239-242, Hilton Head, South Carolina.

Aksenov, et al., Predicting Compensation Voltage for Singly-charged Ions in High-Field Asymmetric Waveform Ion Mobility Spectrometry (FAIMS), Journal of American Society for Mass Spectrometry, Aug. 8, 2012, 1794-1798, 23, American Society for Mass Spectrometry.

Straume, et al., Biomarker-Detection Technologies for Comprehensi8ve Medical Diagnosis During Deep-Space Missions, Recent Patents on Space Technology, Jul. 2013, 13-23, 3, Bentham Science Publishers.

Zamuruyev, et al., Continuous Droplet Removal upon Dropwise Condensation of Humid Air on a Hydrophobic Micropatterned Surface, Langmuir, ACS Publications, Jul. 29, 2014, 10133-10142, 30, American Chemical Society.

* cited by examiner

PORTABLE MEDICAL DIAGNOSIS INSTRUMENT

ORIGIN OF THE INVENTION

The invention described herein was made, in part, by employees of the United States Government and may be manufactured and used by and for the Government of the United States for governmental purposes without the payment of any royalties thereon or therefore.

FIELD OF THE INVENTION

This invention relates to measurement and testing of a chemical compound, provided from a test subject's body, which may contain one or more biomedical markers indicating presence of a medical condition.

BACKGROUND OF THE INVENTION

Extended human exploration missions, such as those planned for Mars and other nearby planetary bodies, will require improved technologies for medical diagnosis and corresponding medical intervention capabilities, because of mission duration (measured in years or decades), distance from the Earth, and the environmental risks involved. Serious health problems that develop on such missions may interfere with mission objectives and could produce mission failure, if capabilities for prompt diagnoses and intervention are not available.

For such missions, performance of rigorous pre-flight medical screening may minimize the risk of serious diseases and injuries. However, such screening cannot eliminate the risk that a serious health condition or injury will occur. Occurrence of known and unknown environmental hazards confronted in space, including but not limited to radiation and loss of bone function in a microgravity environment, cannot be reliably predicted. Medical diagnosis on a future deep space mission (e.g., to Mars and return) must be autonomous and self-sufficient, because of the great distance from an origin on Earth and from interactive health care.

What is needed is an autonomous medical system that anticipates and provides means for diagnosing substantially all serious medical conditions that may arise on a well defined mission. Preferably, the medical system should provide sufficient flexibility that the system can be modified to handle other medical conditions that were not originally anticipated.

SUMMARY OF THE INVENTION

These needs are met by embodiments of the invention, which provides an integrated combination of instruments that receive and analyze different body fluids (e.g., blood, breath, perspiration, saliva and/or urine) from a test subject to estimate one or more medical conditions that may be present in the subject. The instruments that are integrated, in various combinations, comprise the following: (1) a condenser surface that receives a body fluid; (2) an array of functionalized nanostructures (NSs, for example, comprising carbon) that receive the first fluid component, measure changes in one or more electrical parameter values $\Delta EPV$ after exposure of the NS array to the subject's breath or other gases and vapors, and estimate specified components and corresponding concentration values that are present in the first fluid component; (3) a volatilizer (optional) that receives the second fluid component and converts this component partly into gases and vapors and microdroplets; (4) a differential mobility spectrometer (DMS) that receives an ionized portion of the first and/or second fluid components and applies an RF asymmetric electrical field and a compensating electrical field (dc) to transport the chemical component(s) along a longitudinal channel, and to thereby discriminate between ions of different composition; and (5) a biomarker analyzer (optional) that may be a capillary action biomarker analyzer (CABA) mechanism for monitoring presence or absence of one or more target analytes; and/or may be a centrifuge assisted bead sedimentation biomarker analyzer (CASBA) for monitoring presence or absence of one or more target analytes. Each of these instruments provides a different and partly independent physical or chemical perspective on a body fluid that is being tested.

DESCRIPTION OF THE INVENTION

Figure 1:
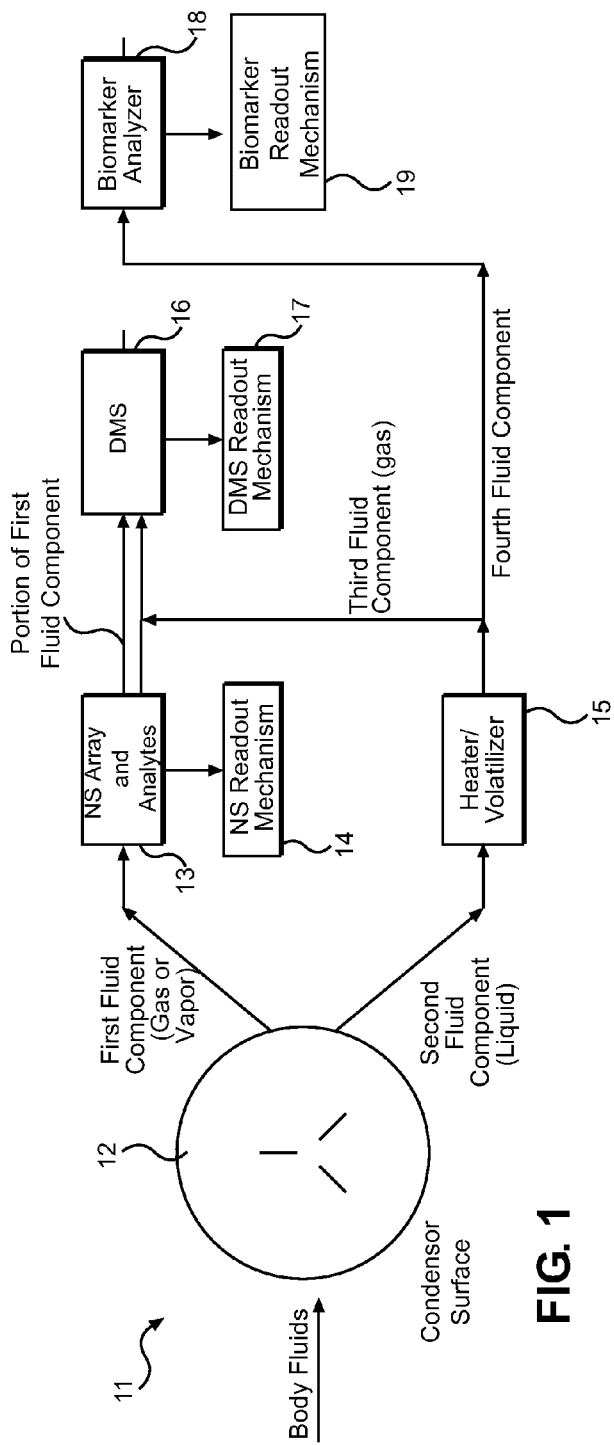
FIG. 1 schematically illustrates embodiments of the invention.

FIG. 1 schematically illustrates embodiments of an integrated system 11 that can be used to measure and analyze one or more body fluid components (e.g., blood count, breath, perspiration, saliva and/or urine) of a subject, to test for presence of one, two or more medical conditions present in the subject. A body fluid is received by a condenser surface 12 and is separated into a first fluid component that is primarily a gas, and a second fluid component that is primarily a liquid. An example of a condenser surface is disclosed in Published U.S. Patent Application 2014/0358023. The condenser surface is applied here only to processing breath.

Figure 2:
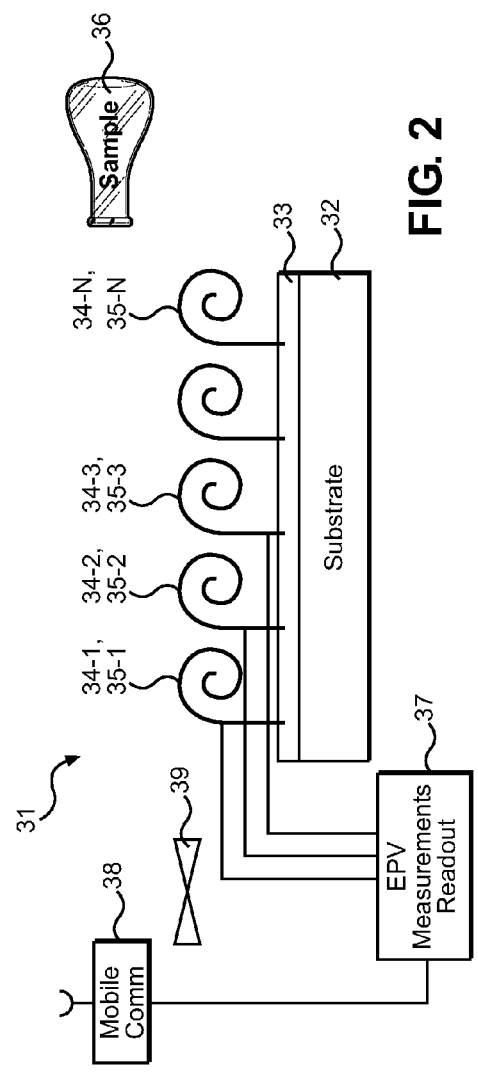
FIG. 2 schematically illustrates an NS array.

A portion of the first fluid component (primarily gas and/or vapor) is received by an array 13 of nanostructures (NSs) and associated NS readout mechanism 14, illustrated in FIGS. 1 and 2, that are preferably functionalized to discriminate between at least first and second specified chemical components, based on measured values in at least one electrical parameter change value $\Delta EPV$. The electrical parameter change value $\Delta EPV$ comprises change in electrical resistance, electrical conductance, electrical impedance, electrical capacitance, electrical inductance, voltage difference or electrical current. The NS array may be functionalized by loading (e.g., doping or impregnating or coating a portion or all of the NSs with a selected dopant or impregnation or coating substance, or by processing the NSs with another suitable procedure. Relevant results from the NS analysis of the first fluid component are received, stored and/or displayed by the readout mechanism 14.

A portion or all of the first fluid component is received by a differential mobility spectrometer (DMS) 16 and associated readout mechanism 17 in FIG. 1 that applies a vertical electrical field, which is asymmetric in time, to discriminate between ions with different molecular compositions, by capturing some ions on side plate electrodes and permitting other ions to pass through and exit from a DMS drift tube.

A portion of the second fluid component is received by a heater/volatilizer mechanism 15 (optional) in FIG. 1 that volatilizes a portion of the second fluid component into a third fluid component (vapor or gas), with the remainder being a fourth fluid component. The volatilized portion (third fluid component) and the first fluid component are received by the DMS 16. The DMS 16 thus separately interrogates the first and second fluid components, and relevant results from the DMS analyses are received, stored and/or displayed by a DMS readout mechanism 17.

The fourth fluid component (primarily liquid) is received by a biomarker analyzer 18 and associated biomarker analyzer readout mechanism 19 (optional). The biomarker analyzer 18 may be a centrifuge Assisted Biomarker Analyzer (CASBA) and/or may be a Capillary Action Biomarker Analyzer (CABA), which are discussed in the following. The CASBA mechanism and/or the CABA mechanism includes a tunable, narrow wavelength range, fluorescence excitation light source and corresponding fluorescence estimator that senses the range of fluorescence wavelengths produced and estimates the corresponding intensity(ies) of the output wavelength(s).

Each of the NS array 13, the DMS 16 and the biomarker analyzer 18 has a readout mechanism, 14, 17 and 19, respectively, that provides at least one of a numerical readout and/or a visual readout of relevant Z/m data.

The first fluid component may include gases from breath, from perspiration, from saliva, and from urine, among others. The second fluid component may include liquids from blood, from perspiration, from saliva and from urine, among others. As noted, the condenser surface is applied only to process breath.

FIG. 2 schematically illustrates a measurement system 31 that provides functionalized nanostructures ("NSs") as part of the invention. The measurement system 31 includes: a substrate 32; an appropriate catalyst underlayer 33 (optional); a sequence of distinct sub-arrays 34-$n$ ($n=1, \ldots, N$; $N \geq 3$) of NSs deposited or grown on the substrate 32; a selected "loading" (doping, impregnation, coating, non-functionalized, etc.) 35-$n$ of an NS sub-array 34-$n$; a source 36 of a sample gas or vapor to be interrogated; an EPV measurement and readout mechanism 37 for measuring, analyzing, storing and/or displaying one or more electrical parameter values EPV(n;meas.t) or EPV change values $\Delta$EPV(n;meas;t) at each of the N NS sub-arrays, before and after exposure of that sub-array to the sample gas; a mobile communication mechanism 38 (optional), including a computer that is programmed to receive the sequence of measured electrical parameter values, EPV(n;meas;t), or EPV change values, $\Delta$EPV(n;meas;t), to compare the measured values with corresponding reference values EPV(n;ref), and to estimate whether a specified chemical or component is likely present in the sample gas; a most probable concentration value (if the specified component is likely present in non-negligible concentration); and a system refresh mechanism 39 (optional), to refresh and reset the NS sub-arrays for subsequent measurements, in a time interval, preferably with length no more than about 15-30 sec. Each NS sub-array 34-$n$ may consist of a single NS or may include two or more NS s with the same functionalization. Two different NS sub-arrays, 34-$n$1 and 34-$n$2, may have the same number, or a different number, of NSs. For some sample gases, the response time for detection may be no more than about 2-5 sec; and/or the minimum detection value may be as low as 5 ppbv (parts per billion by volume; e.g., $NO_2$, with a detection limit of about 4.6 ppbv at T=25° C.). Response time for detection of other gases at a detection limit (minimum measurable concentration value) may be greater. Embodiments of the system 31 are discussed in more detail in U.S. Pat. Nos. 7,801,687 and 8,000,903, issued to Jing Li et al and incorporated by reference herein.

Nanostructure Measurement Procedure.

Up to 32 individually functionalized NS channels in the system 31 were initially tested and confirmed to work as expected. This number has been increased to an array of 64 channels (1 cm×1 cm size), and will be increased further as the perceived need increases, limited only by considerations such as chip size, interconnections, and signal-to-noise ratio. An array of 32 NS channels has been reduced in size to that of a postage stamp, which can fit into, and provide connections to, a mobile communication system (optional; disclosed in U.S. patent application Ser. No. 13/896,271, incorporated herein by reference).

The surface area per unit mass for the NS is very high, up to about 1580 $m^2$/gm in one embodiment, so that the EPV change value $\Delta$EPV is quite sensitive to presence of even a small amount of a specified chemical or component. For example, presence of nitrogen dioxide ($NO_2$) at a concentration of 4.6 ppbv has been detected using one NS sub-array. With an appropriate choice of differently functionalized NSs, the NS sub-array can collectively distinguish between presence of two or more different specified components and can provide an estimate of most probable concentration value, for each component that is present above a detection threshold concentration. Thus far, we have tested our functionalized NS array on more than 15 different specified components, including ammonia ($NH_3$), nitrogen dioxide ($NO_2$), hydrogen chloride (HCl), chlorine ($Cl_2$), hydrogen cyanide (HCN), hydrogen peroxide ($H_2O_2$), hydrazine ($N_2H_4$), methane ($CH_4$), benzene ($C_6H_6$), acetone (($CH_3$)$_2$CO), formaldehyde ($CH_2O$), toluene ($C_6H_5(CH_3)$), dinitrotoluene (DNT), and some nerve agents and simulants thereof, such as sarin, soman, and dimethyl methylphosphonate (DMMP). As the number of different specified components being tested increases, the required number of separately functionalized NSs also increases. The sensors constructed using the functionalized NSs are robust, long lasting (at least three years lifetime), will operate in the presence of high intensity vibrations, and the measured values can be compensated for varying temperature, varying humidity and varying pressure.

An NS array or sub-array can be recycled or refreshed, after its use for a particular gas, by at least two methods: (1) local heating of the NS array to temperatures of about 120° C. for about 10-15 min and/or (2) irradiation of the NS array with ultraviolet-emitting LEDs (e.g., with wavelengths in a selected range, such as $\lambda$=254-256 nm, for several seconds.

The particular electrical parameter change value $\Delta$EPV (n;meas;t), measured for each of the functionalized or non-functionalized sensor sub-arrays, may be electrical resistance, electrical conductance, electrical capacitance, electrical inductance, voltage difference, electrical current, or some other relevant, measurable electrical value. For electrical current, for example, the change values $\Delta$EPV(n; meas;t) are often measured in $\mu$Amps or in mAmps.

Figure 3A:
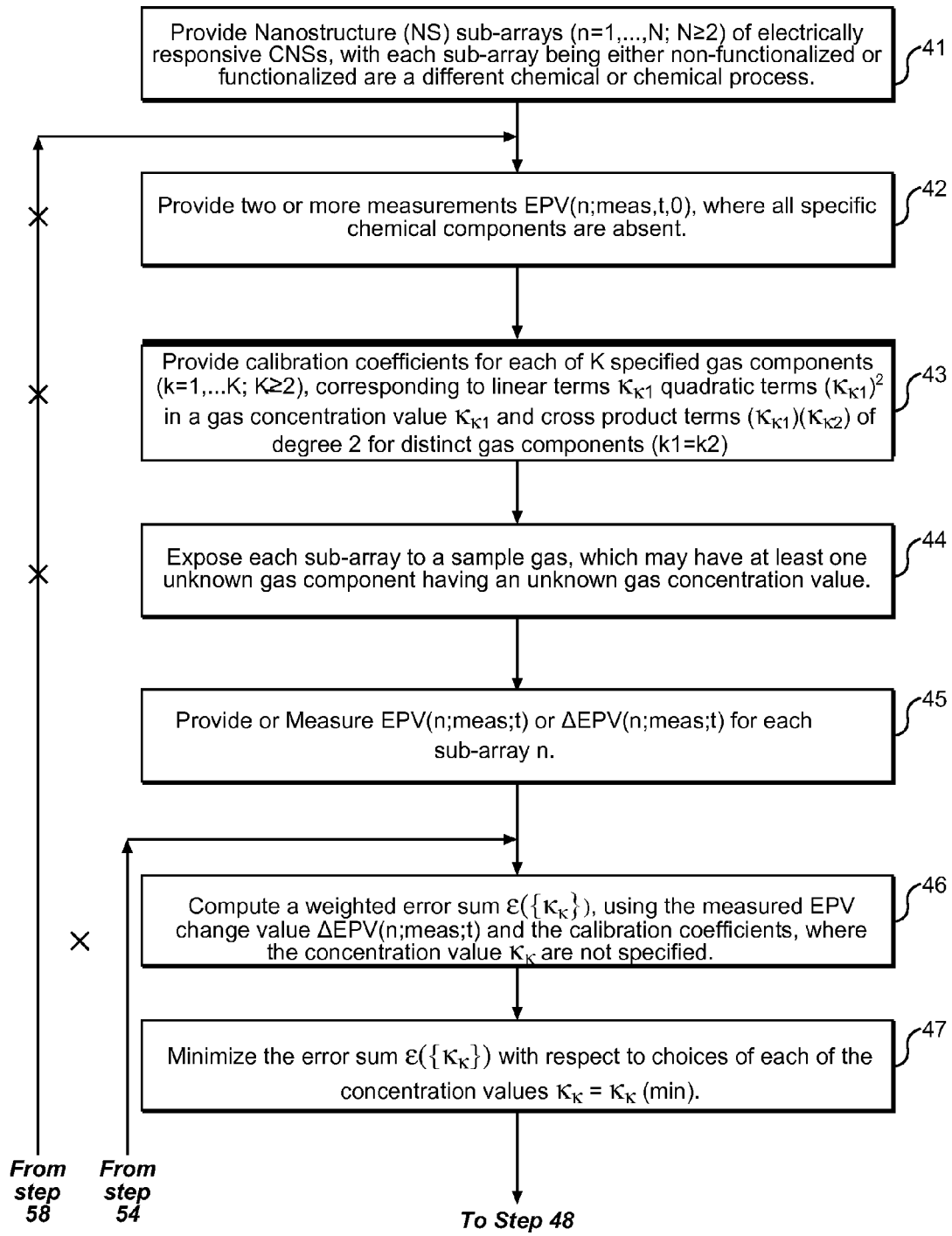
FIG. 3A-3C show a flowchart illustrating operation of an NS array.
Figure 3B:
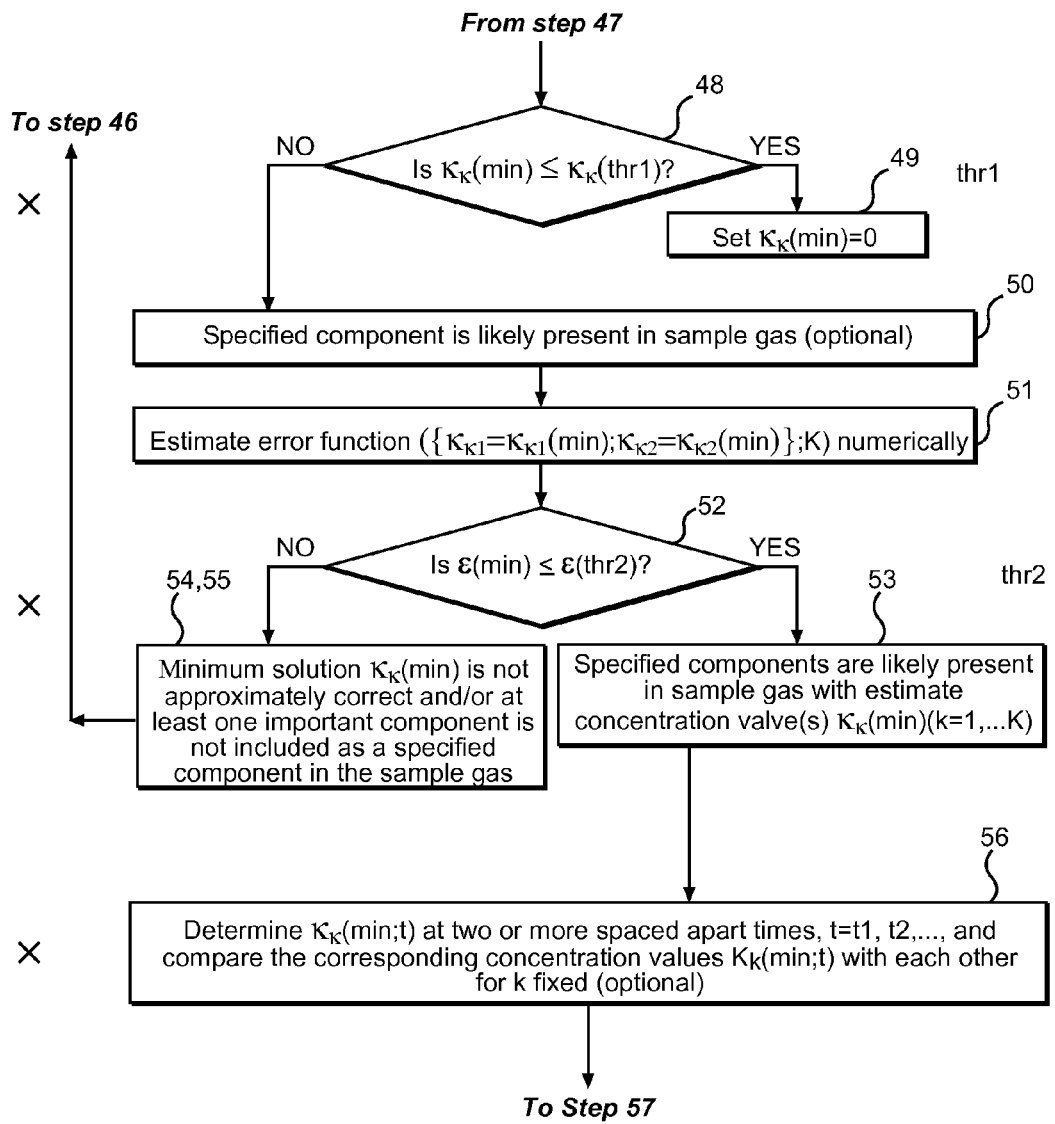
Figure 3C:
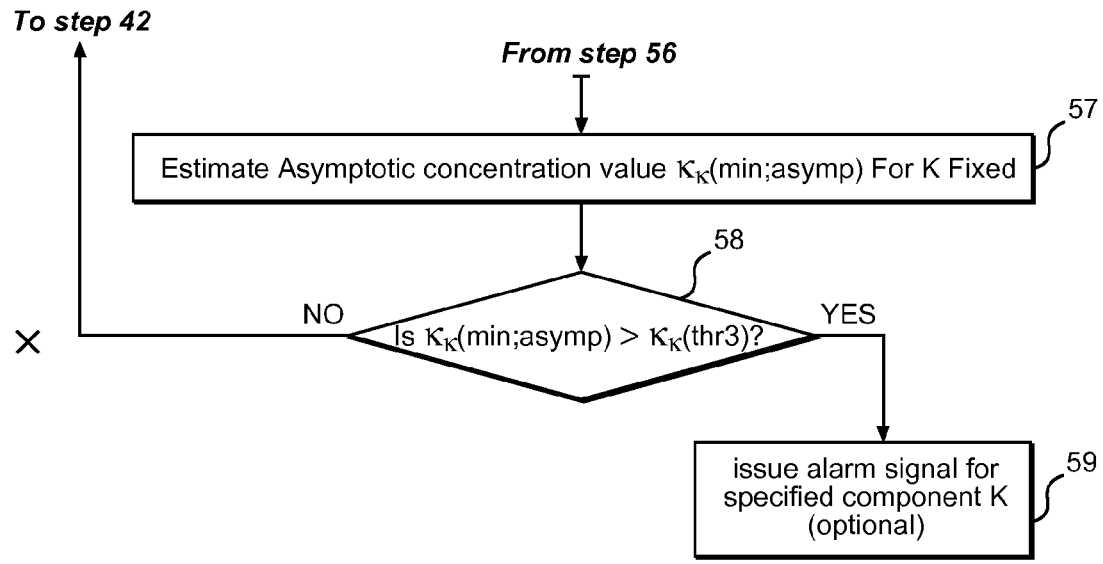

FIGS. 3A-3C is a flow chart illustrating a suitable procedure for practicing the invention using the system 31.

Step 41: Provide N nanostructure ("NS") sub-arrays, numbered $n=1, \ldots, N$ ($N \geq 2$), on a substrate, where each NS sub-array is either not functionalized or is functionalized with a selected functionalizing substance or process, where each NS sub-array comprises at least first and second interdigitated electrodes, with the first and second electrodes being connected at a first end to at least one of (i) a controllable voltage source and (ii) a controllable current source, and with the first and second electrodes being connected in an electrical path to each other through one or more of the NS sub-arrays.

Step 42: Provide at least one measurement (preferably, at least two measurements) of an electrical property value EPV(n;meas;t;0) for n=1, . . . , N, where all specified components are absent, but other ambient components may be present, where an EPV value, measured at a particular sensor sub-array (n) and corresponding to a single specified component (m1) is approximated by a constitutive relation, $$EPV(n;k1;\text{meas})=a_0(n)+b_{k1}(n)\kappa_{k1}+c_{1,1}(n)\kappa_{k1}^2, \quad (1)$$

where $\kappa_{k1}$ is a value of concentration of the specified component k1 and $a_0(n)$ represents EPV response where no specified component or analyte is present. Where two or more specified components, numbers k=k1 and k2, are present, an expanded constitutive relation for the combined specified components is used, $$EPV(n;k1,k2;\text{meas})=a_0(n)+b_1(n)\kappa_{k1}+b_2(n)\kappa_{k2}+c_{1,1}(n)\kappa_{k1}^2+c_{2,2}(n)\kappa_{k2}^2+d_{1,2}(n)\kappa_{k1}\kappa_{k2}, \quad (2)$$

where $d_{1,2}(n)$ is a cross product term associated with the concentration cross product, $\kappa_{k1}\kappa_{k2}$. ($\kappa_{k1} \neq \kappa_{k2}$).

Step 43: Provide calibration coefficients $a_0(n)$ (optional), $b_k(n)$, $c_{k,k}(n)$ and $d_{k1,k2}(n)$, for the sub-array number n= 1, 2, . . . , N for the K specified components, numbered k=k1, k2=1, . . . , K, with k1≠k2 and K≥1 (preferably K≥2). The calibration coefficient $a_0(n)$ is associated with the measured value EPV(n;meas;t;0) for n=1, . . . , N. Where one works with a measured EPV change value, defined as $$\Delta EPV(n;\text{meas};t)=EPV(n;\text{meas};t)-EPV(n;\text{meas};t;0), \quad (3)$$

the calibration coefficient $a_0(n)$ need not be used in modeling ΔEPV behavior for a particular specified component.

For arbitrary concentration values $\kappa_k$ of one or two specified components (k=k1, k2=1, . . . , K; K=1 or 2), it is assumed that the measured change value ΔEPV(n;meas;t) for a given sub-array (n) can be expressed or approximately modeled as a nonlinear combination of the concentrations $\kappa_1$ and $\kappa_2$, $$\Delta EPV(n;k1,k2;\text{model};t)=b_1(n)\kappa_{k1}+b_2(n)\kappa_{k2}+c_{1,1}(n)(\kappa_{k1})^2+c_{2,2}(n)(\kappa_{k2})^2+2d_{1,2}(n)(\kappa_{k1})(\kappa_{k2}), \quad (4)$$

for (postulated) presence of two specified components with the associated concentrations, $\kappa_1$ and $\kappa_2$, where n refers to the particular NS sub-array. Where a value EPV(n;meas;t) is used, the coefficient $a_0(n)$=EPV(n;meas;t;0) is also included in the right hand sum in Eq. (2). Inclusion of a cross-product term, $d_{1,2}(n)(\kappa_1)(\kappa_2)$, accounts for interaction of at least two distinct components. The calibration coefficients, $a_0$, $b_k$, $c_{k,k}$ and $d_{k1,k2}$ (k=k1 or k2), are estimated or determined experimentally for a single specified component or pairs of specified components. Optionally, the NS array may include sensors for one or more environmental values, such as temperature, humidity and/or pressure. The calibration coefficients, $a_0$, $b_{k1}$, $b_{k2}$, $c_{k1,k1}$, $c_{k2,k2}$ and $d_{k1,k2}$, in Eq. (4), can be compensated for variation of one or more of these environmental variables, using, for example, techniques disclosed in U.S. Pat. No. 8,000,903, issued to Jing Li and incorporated herein by reference.

Where only one specified component (e.g., $\kappa_{k1}$) is postulated to be present, the coefficients $b_{k2}(n)$, $c_{k2,k2}(n)$ and $d_{k1,k2}(n)$ are preferably set equal to 0. The nonlinear combination of concentration values in Eq. (2) can be extended to presence of K (≥2) components, with an increase in the experiments needed to determine the total number, (K+1)(K+2)/2, of calibration coefficients needed, but the computations are much more complex. For K=1 and K=2, the maximum numbers of calibration coefficients required are 3 and 6, respectively.

Step 44: Expose the NS sub-arrays for a selected time interval to a sample gas, which may contain, but need not contain, one or more of the specified components, where the sample gas is to be examined for presence or absence of each of K specified components, numbered k=1, . . . , K.

Step 45: Provide or measure electrical property change values ΔEPV(n;meas;t), defined in Eq. (3), between the first and second electrodes in the NS sub-array number n=1, . . . , N, as a result of exposure of the NS sub-array number n to the sample gas, where each EPV change value, ΔEPV(n;meas;t), is drawn from the group of change values consisting of electrical current, voltage difference, resistance, impedance, conductance and capacitance, measured between the first and second electrodes in the NS sub-array number n.

Step 46: For K≥2, form a non-negative error sum $$\varepsilon(\{\kappa_{k1}, \kappa_{k2}\}; K) = \sum_{n=1}^{N} w_n |\Delta EPV(n;\text{meas};t) - \Delta EPV(n;\text{model};t)|^p, \quad (5)$$

from weighted differences between the measured change values ΔEPV(n;meas;t) and an estimate of the modeled EPV change values computed using the calibration coefficients, with specified gas component concentrations $\kappa_\kappa$ ((k=1, . . . , K) that are not yet known. Here, $\{w_n\}$ are non-negative weight coefficients, at least one being positive, and p is a selected positive number (e.g., p=1 or 1.62 or 2 or √17 or any other rational or non-rational number).

Step 47: Minimize the error function sum for choices of each of the concentration values, $\kappa_{k1}$ and $\kappa_{k2}$, to obtain estimates of minimum-solution concentration values, $\kappa_k = \kappa_k$(min) (k=k1, k2) that together provide a minimum numerical value $\epsilon$(min) for the error sum $\epsilon(\{\kappa_{k1},\kappa_{k2}\};K)$ in Eq. (5).

Step 48: Where an estimated minimum-solution concentration value $\kappa_k$(min) is no greater than a selected threshold concentration value $\kappa_k$(thr1) for the specified gas component, k, in step 48, interpret this condition as indicating that the specified component k is present in the sample gas, if at all, in a negligible concentration ($\kappa_k$(min)≈0).

Step 49: Set the concentration value $\kappa_k$ equal to 0 (optional), if the condition in step 48 is satisfied for a particular specified component number k.

Step 50: Where an estimated minimum-solution concentration value $\kappa_k$(min) is greater than the selected threshold concentration value $\kappa_k$(thr1) for the specified gas component k, interpret this condition as indicating that the specified component k is present in the sample gas with an estimated concentration $\kappa_k$(min), (optional).

Step 51: Numerically evaluate or estimate the error function, $\epsilon$(min)=$\epsilon(\{\kappa_{k1}=\kappa_{k1}$(min); $\kappa_{k2}=\kappa_{k2}$(min)$\};K)$, for each concentration value $\kappa$ equal to its minimum-solution value, $\kappa_k = \kappa_k$(min).

Step 52: Compare the minimum error value $\epsilon(\{\kappa_{k1}=\kappa_{k1}$(min); $\kappa_{k2}=\kappa_{k2}$(min)$\};K)$=$\epsilon$(min) to a selected threshold error value, $\epsilon$(thr2).

Step 53: Where the minimum error value $\epsilon(\{\kappa_{k1}=\kappa_{k1}$(min); $\kappa_{k2}=\kappa_{k2}$(min)$\};K)$ is no greater than a selected error threshold $\epsilon$(thr2), interpret this condition as indicating that the specified components are likely to be present in the sample gas, with concentration values approximately equal to the minimum-solution values $\kappa_k$(min).

Step 54: Where the minimum error value $\epsilon(\{\kappa_{k1}=\kappa_{k1}(\min); \kappa_{k2}=\kappa_{k2}(\min)\};K)$ is greater than the selected error threshold value $\epsilon(\text{thr2})$, interpret this condition as indicating that either (i) the minimum-solution concentration value is not approximately correct for at least one specified sample gas component (k=1, . . . , K), and/or (ii) at least one important gas component that is present is not included as a specified component in the sample components.

Step 55: Where the query in step 54 is answered "yes," include at least one additional gas component in the list of specified gas components and include additional calibration coefficients for one or more additional sample gas components in the specified components list, for each of the arrays n=1, . . . , N, and return to step 43 (optional).

Step 56: Estimate the minimum-solution concentration values, $\kappa=\kappa_k(\min;t)$, at two, three or more spaced apart measurement times, t=t1, t2(>t1), t3(>t2), etc., and compare the corresponding concentration values, $\kappa_k(\min)$ (k fixed; t variable), with each other for the measurement times.

Step 57: Where the corresponding minimum-solution concentration values $\kappa k(\min;t)$ are substantially different from each other for two or more spaced apart measurement times (e.g., the absolute value of the difference for fixed k is greater than a positive threshold difference), estimate an asymptotic minimum-solution concentration value, $\kappa_k=\kappa_k(\min;\text{asymp})$ for that specified chemical (optional), using a first order or second order chemical reaction model, and (optionally) make this asymptote available for at least one recipient. Preferably, an asymptotic estimate, $\kappa_k=\kappa_k(\min;\text{asymp})$, is promptly estimated, where the specified component and its concentration value may be a concern for human health or safety.

Step 58: The system determines if the predicted asymptotic concentration value, $\kappa_k(\min;\text{asymp})$, or the present concentration value $\kappa_k(\min;t)$, is at least equal to a selected alarm-threshold concentration value $\kappa_k(\text{thr3})$.

Step 59: When the answer to the query in step 58 is "yes," the system promptly issues an alarm signal to advise interested users of the system that the present or predicted asymptotic concentration value for at least one gas of concern is, or will soon be, above the alarm-threshold concentration value, $\kappa_k(\text{thr3})$.

Optionally, the system compares the minimum-solution concentration value, $\kappa_k(\min)$, with the threshold concentration value $\kappa_k(\text{thr3})$ for first and second sampling times, and monotonically decreases a separation time between the first and second sampling times when (i) the minimum-solution concentration value is less than the threshold concentration value, $\kappa_k(\text{thr3})$, and (ii) the minimum-solution concentration value appears to asymptotically approach, or to exceed, the threshold concentration value $\kappa_k(\text{thr3})$. This provides a finer measure of approach of $\kappa_k(\min;t)$ to an asymptotic value.

For a choice of K=1 specified component, no cross product terms are present in a constitutive relation, and the calibration coefficients $a_0(n)$, $b_1(n)$ and $c_{1,1}(n)$ may be determined by a quadratic regression process. Assume that a collection of measurements $EPV(n;\text{meas};\kappa_k;t)$ (k=1, . . . , K; K≥2) is provided, with corresponding known concentration values $\kappa_k$). An error function $$\varepsilon(a_0(n), b_{k1}(n), c_{k1,k1}(n)) = \qquad (6)$$

$$\sum_{k1=1}^{K} \{a_0(n) + b_1(n)\kappa_{k1} + c_{1,1}(n)\kappa_{k1}^2 - EPV(n;\text{meas};\kappa_{k1};t)\}^2$$

is minimized with respect to choices of the calibration coefficients $a_0(n)$, $b_1(n)$ and $c_{1,1}(n)$. This yields three coupled equations in these coefficients:

$$\sum_{k1=1}^{K} \{a_0(n) + b_1(n)\kappa_{k1} + c_{1,1}(n)\kappa_{k1}^2 - EPV(n;\text{meas};\kappa_{k1};t)\}\{1\} = 0, \qquad (7A)$$

$$\sum_{k1=1}^{K} \{a_0(n) + b_1(n)\kappa_{k1} + c_{1,1}(n)\kappa_{k1}^2 - EPV(n;\text{meas};\kappa_{k1};t)\}\{\kappa_{k1}\} = 0, \qquad (7B)$$

$$\sum_{k1=1}^{K} \{a_0(n) + b_1(n)\kappa_{k1} + c_{1,1}(n)\kappa_{k1}^2 - EPV(n;\text{meas};\kappa_{k1};t)\}\{\kappa_{k1}^2\} = 0, \qquad (7C)$$

whose joint solutions $\kappa_{k1}$ for each NS array (n) can be estimated.

Inclusion of additional terms in Eq. (2), beyond second degree in the concentration values $\kappa_k$, is possible but tedious and requires additional experiments and reference measurements. The model adopted in Eq. (2) includes the lowest order effects of linear and quadratic dependences upon individual concentration values $\kappa_k$ and of lowest order cross product terms, such as $(\kappa_{k1})(\kappa_{k2})$. Preferably, functionalizations for the different NS sub-arrays are chosen so that no two sets of calibration coefficients, $(a_0(n1), b_k(n1), c_{k,k}(n1), d_{k1,k3})(n1))$ and $(a_0(n2), b_{k2}, (n2), c_{k2,k2}(n2), d_{k2,k4})(n2))$, are approximately proportional to each other for $n1 \neq n2$.

Given N sub-arrays of NS sensors and a set of K specified components, numbered k=1, . . . , K (K=1, 2, . . . )), the measured EPV change data for the sensors can be pre-processed in order to identify more clearly which functionalized NS sensor sub-arrays are more sensitive to presence of a particular specified component. In a first embodiment, the sub-array is exposed to a selected component (k) of a gas of concern (e.g., liquid explosive, toxin, poison or nerve agent), for example, $CO_2$, $NH_3$, $NO_2$, $Cl_2$, HCl, HCN, $H_2O_2$, $N_2H_4$ (hydrazine), $CH_4$ (methane), $C_6H_5(CH_3)$ (toluene), $C_6H_6$ (benzene), $(CH_3)_2CO$ (acetone), DNT (dinitrotoluene, $CH_2O$ (formaldehyde), DMMP (dimethyl methylphosphonate), sarin, soman and/or other gases, at a selected sequence of two or more concentration values $\{\kappa_k(q)\}_q$ (q=1, . . . , Q with $1 \leq Q \leq N$) of Q different, specified concentration values, and a reference measurement value, $EPV(n; \kappa_k(q);\text{ref})$ (n=1, 2, . . . , N), is recorded for each sensor sub-array n and for each known concentration $\kappa_k(q)$ of a reference gas containing a specified component (k). Some of these gases appear simultaneously, as separate components and in an assembled molecule(s), so that, whenever a characteristic component is found, presence of the other components and of the corresponding assembled molecule should also be queried.

Differential Mobility Spectrometer.

Figure 4:
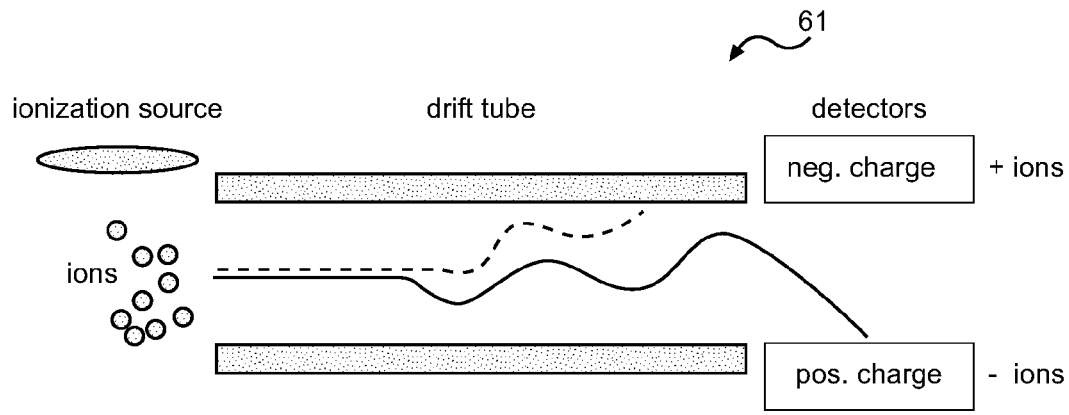
FIG. 4 illustrates operation of a DMS instrument.

FIG. 4 schematically illustrates operation of one embodiment of a differential mobility spectrometer (DMS) 61 for use in the invention. The diagnostic device 61 comprises a drift tube, an ionization source and a source of ions at a first end of the drift tube; and first and second ion detectors for respective negatively charged and positively charged ions located at a second end of the drift tube. Optionally, the device also includes one or more sources of a compensating electrical (CE) field that can be individually or collectively varied with time to discriminate between ions with different mass-to-charge ratios m/Z, different sizes and different shapes or collision cross-sections, collectively referred to as differential mobility parameters The device uses mobility differences of chemicals in high strength, asymmetric electrical fields to separate and provide identifying information for the compounds. Typically, the device has a longitudinal length of 10-100 cm, a diameter of 5-10 mm, and an applied electrical field strength |E| of 5-300 Volts/mm, but may be larger or smaller. Here, the device is miniaturized.

Use of the device for breath analysis is discussed in the following disclosures, which are incorporated by reference herein: M. Schivo et al, Jour. Of Breath Research 7(1): 017113 doi: 10.1088/1752-7155/7/1/017113; C. E. Davis et al, IEEE Sensors Jour., Special Issue, "Sensors For Breath Analysis" vol. 10, pp. 114-122, 2010; C. E. Davis et al, IEEE Sensors Jour., Special Issue, "Sensors For Breath Analysis" 10(1) 3-6; M. Molina et al, Analytica Chimica Acta, vol. 628, pp. 155-161, 2008.

Capillary Action Biomarker Analyzer (CABA).

Figure 5:
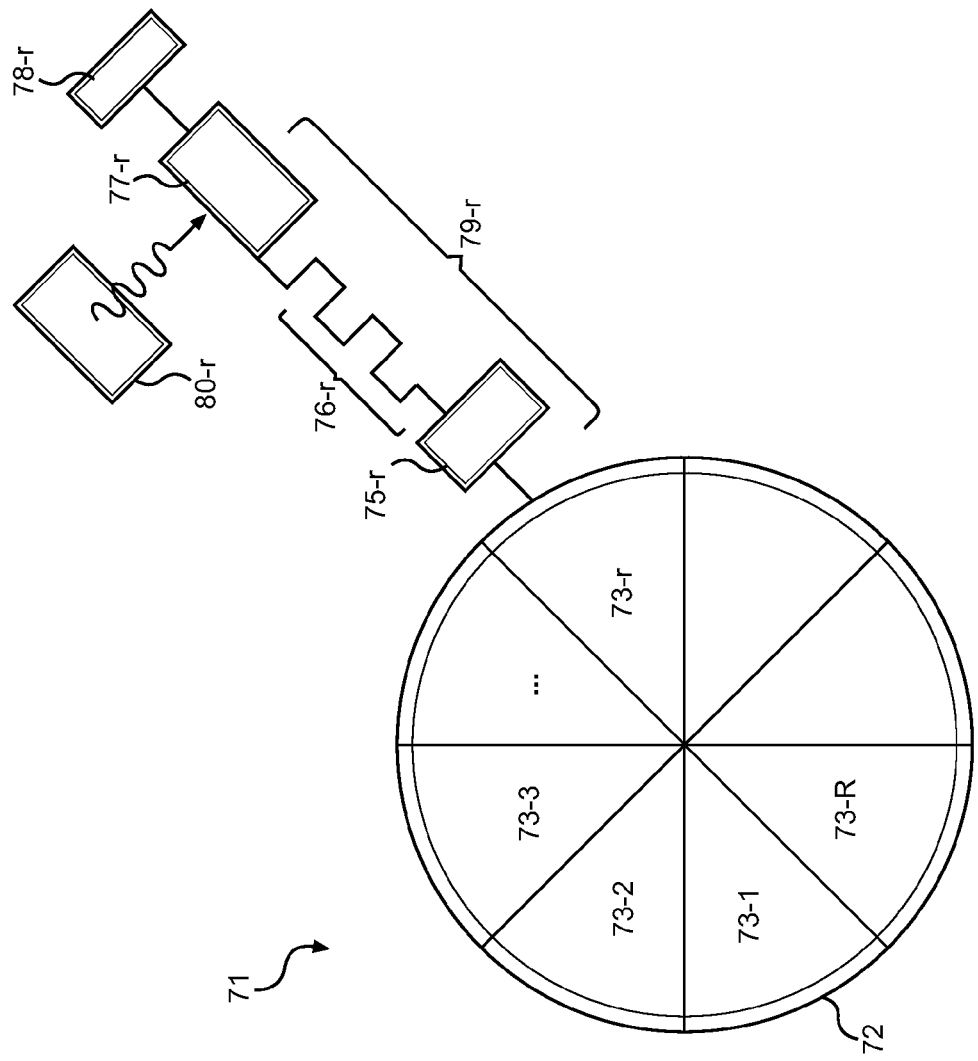
FIG. 5 illustrates a mechanism using controlled capillary flow to estimate the presence or absence of a specified substance (analyte) of interest.

A Capillary Action Biomarker Analyzer (CABA) system 71, illustrated in FIG. 5, uses microfluidic flow of captured and detected antibodies in controllable capillaries to isolate and identify biological substances of concern that may be presented in certain medical conditions, using a modified ELISA procedure. A microfluidic transport and display card and reader is provided with a central entry port region 72 that receives a liquid sample LS, usually a few drops. The entry port 72 is connected to each of R separate channels 73-$r$ ($r=1, \ldots, R$) that serve as entry channels for the sample. The liquid sample LS may include a target substance TS-r, whose presence or absence is to be assessed.

A portion of the sample LS in channel 73-$r$ moves into a mixing chamber 75-$r$ that contains at least one capture antibody CAB-r that is sensitive to, and binds with, the target substance TS-r. If the target substance TS-r is contained in the sample LS, some molecules of the capture antibody CAB-r and the target substance TS-r will combine as a plurality of mobile CAB-r/TS-r complexes in the mixing chamber 75-$r$ and/or in a serpentine capillary action channel 76-$r$ that receives and transports output from the mixing chamber 75-$r$. A detection and viewing chamber 77-$r$ contains detection antibody molecules DAB-r that are bound or otherwise attached to a substrate that is part of the chamber 77-$r$. The detection and viewing chamber 77-$r$ receives the output CAB-r/TS-r complexes from the serpentine capillary action channel 76-$r$.

The detection antibodies DAB-r have been conjugated with a photosensitive labeling agent, such as a fluorescent molecule or colorimetric label; and some of the mobile CAB-r/TS-r complexes, if present, will combine with the immobilized DAB-r antibodies and form an immobilized, photosensitive-labeled, CAB-r/TS-r/DAB-r complex. The contents of the detection and viewing chamber 77-$r$ that are not immobilized are carefully washed away. Only the immobilized CAB-r/TS-r/DAB-r complexes, if any, remain in the detection and viewing chamber 77-$r$.

The serpentine capillary action channel 76-$r$, the detection and viewing chamber 77-$r$ and a wicking pad or pump 78-$r$ (optional) form a transport channel 79-$r$ for the CAB-r/TS-r complex. After the CAB-r/TS-r/DAB-r complex has formed and become immobilized in the detection and viewing chamber 77-$r$, a light source 80-$r$, having a narrow wavelength range ($\lambda_{1,r} \leq \lambda \leq \lambda_{2,r}$), is activated and illuminates the contents of the detection and viewing chamber 77-$r$.

When and only when, upon such illumination, some molecules in the CAB-r/TS-r/DAB-r complex in the viewing and detection chamber 77-$r$ are activated and emit fluorescence or other radiation in an expected narrow wavelength range and with an intensity at least equal to a selected threshold intensity, the system concludes that the target substance TS-r is present in the liquid sample. When, in response to such illumination, the contents of the detection and viewing chamber 77-$r$ do not emit radiation in the expected wavelength range, or appear with a radiation intensity below the selected threshold intensity, the system concludes that the target substance TS-r is not present in the liquid sample LS. In this CABA mechanism, after the unknown sample and the capture antibody CAB-r combine as a complex, this complex is mobile, not localized. Subsequent interaction of this complex with an immobilized detection antibody DAB-r causes immobilization of the CAB-r/TS-r/DAB-r complex, for purposes of detection.

The contents of the detection and viewing chamber 77-$r$ are carefully washed. The molecules of liquid sample LS and capture antibody CAB-r that are not immobilized in the detection and viewing chamber 77-$r$, are removed from the system.

The system 71 can be configured to interrogate the liquid sample LS with light in each of R narrow, preferably non-overlapping wavelength ranges, $\lambda_{1,r} \leq \lambda \leq \lambda_{2,r}$ ($r=1, \ldots, R$; $R \geq 2$), in order to confirm or refute the hypothesis that one or more of the target substances TS-r($r=1, \ldots, R$) is, or is not, present in the liquid sample LS. If R separate channels 73-$r$ are provided, presence of as many as R different target substances can be simultaneously tested; or contemporaneous appearance of radiation for two or more distinct wavelength ranges for the same biomarker can be sensed to provide further confirmation of presence of the target substance TS-r.

Apart from a small amount of energy used in providing the activation wavelength, no electrical power is required here for this alternative. Rate of delivery of the CAB-r/TS-r complex to the detection and viewing chamber 77-$r$, is partly controlled by choices of effective diameter and effective length of the transport channels 79-$r$.

Centrifuge Assisted Sedimentation Biomarker Analyzer (CASBA).

Another procedure for analyzing composition and estimating concentration of blood components uses a novel sedimentation approach to conduct bead-based ELISA-type sandwich immunoassays in a circular disk (CD)-based centrifugal microfluidics device. The CD contains fluorescently labeled "detection" antibodies in the sample-loading chamber. The disk also contains density centrifugation media in the separation zone. In one embodiment, a fluid such as whole blood or saliva is loaded into the disk, using a disposable plastic pipette or capillary tube and incubated for a few minutes. The CD is spun to separate the beads from unreacted reagents and sample. An optical detector reads the fluorescent signal from the sediment beads. Multiple analytes can be detected in minutes from a single drop of fluid. Advantages of the device sample analysis include the following: further miniaturization is available; sample-to-answer procedure can be performed in less than 15 minutes; high analytical sensitivity; and ability to multiplex, with 16 to 32 assays per CD. The analyzer does not require sample preparation before the sample is loaded into the device so that the device can be adapted for space applications.

Details of the approach are discussed in the following articles, which are incorporated by reference herein: U. Y. Schaff et al, Clinical Chem., vol. 57, pp 753-761, 2011; G. Sommer et al, "Microfluidic Devices, Systems and Methods for Quantifying Particles Using Centrifugal Force," U.S. patent application Ser. No. 12/891,956, September 2010; G. Sommer et al, "Devices, Systems and Method for Conducting Sandwich Assays Using Sedimentation,", U.S. patent application Ser. No. 12/891,977, September 2010; G. Sommer et al, "Systems, Devices and Methods for Agglutination Assay," U.S. patent application Ser. No. 13/423,073, March 2012; G. Sommer et al, "Rapid Sensitive Detection & Quantification of DNA in Clinical Samples," U.S. patent application Ser. No. 13/423,008, March 2012; G. Sommer et al, "Devices, Systems and Methods for Conducting Assays," U.S. patent application Ser. No. 13/423,050, September 2012; G. Sommer et al, "Quantitative Detection of Pathogens in Centrifugal Microfluidic Disks," U.S. Patent Appl. 61/673,373, July 2012.

An ELISA procedure is applied to sedimentation of functionalized or sensitized particles, some of which may be bound to a sample containing the target substance (e.g., an antigen). The procedure is preferably performed in a density medium in which the density p(part) of an individual sedimentation particle is greater than the density p(medium) of the density medium, which is greater than a density p(part-sample;avg) of a combined (averaged) particle-sample complex p(part-sample).

The mixture is preferably centrifuged to separate the heavier particle-plus-complex from the lighter density medium. Response of the labeled detection agent(s) is analyzed, by photo-excitation of the detection label DL, to confirm or refute the postulated presence of the target substance TS bound on some or all of the sedimentation particles. Photo-excitation will appear only where a detection label DL with a corresponding wavelength-activation range is present; and if present, the signal intensity will be approximately proportional to concentration of the target substance TS. Using Stokes law, the sedimentation rate for the particles is proportional to a difference between p(part) and p(medium).

Pathways for Identification.

Figure 6:
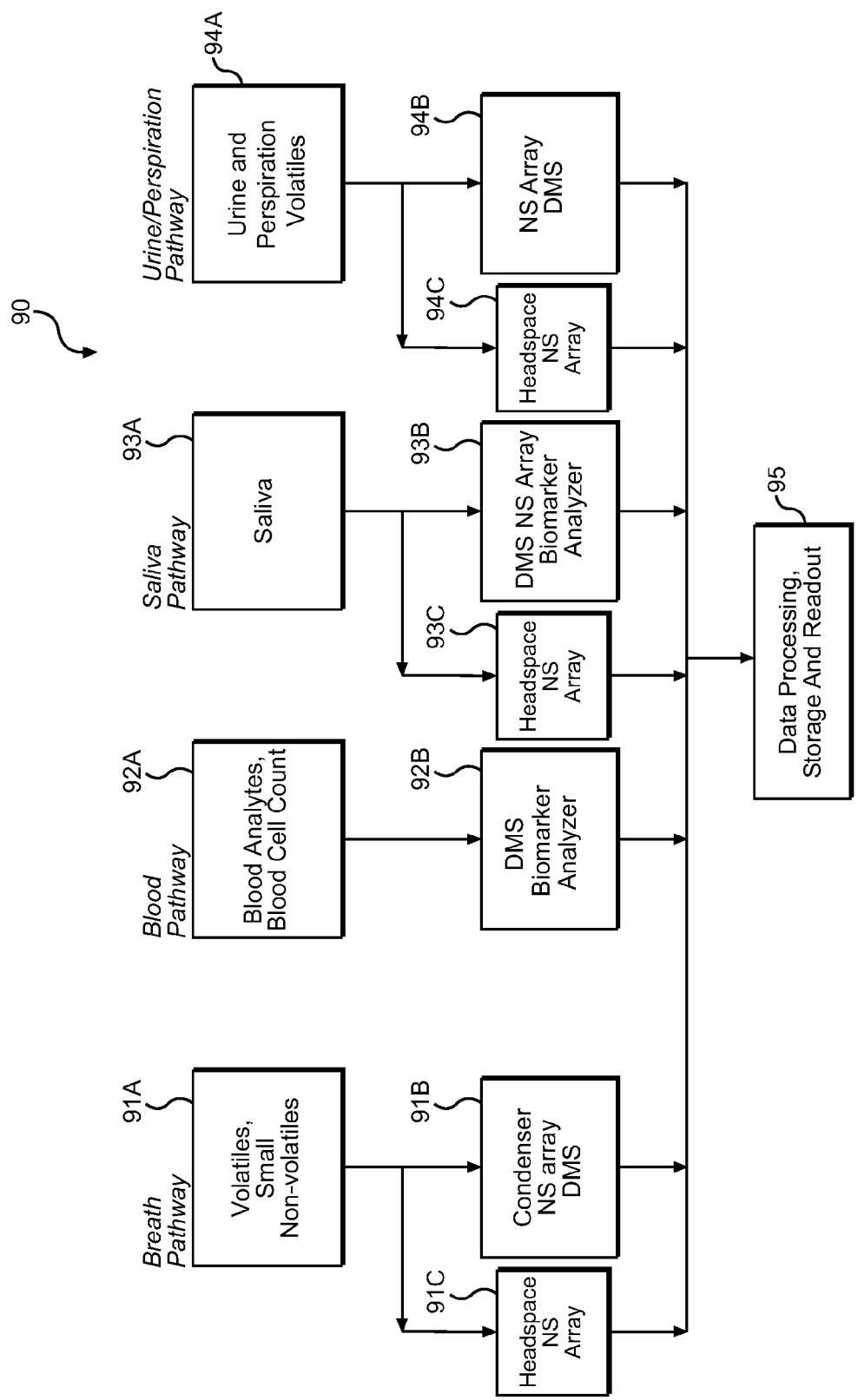
FIG. 6 illustrates pathways for detection of analytes.

FIG. 6 illustrates some of the individual pathways for identification and analysis of different chemicals, analytes and/or antigens that are present in a sample. This characterization focuses on a "carrier" and the most useful technologies for the target chemicals, analytes and/or antigens: volatiles, small non-volatiles, blood analytes, blood cell counts, breath, perspiration, saliva and urea. This characterization extends to pathways for perspiration and for urine (urea is found in both, if the measurement is taken within two hours of urine excretion), which may include additional components analogous to the blood components found in breath, in perspiration, in saliva, and/or in urine. As noted, use of the condenser is limited to processing of breath.

The system 90 of pathways comprises one or more of the following. A breath pathway module 91A receives volatiles and small non-volatiles and passes this substanc(es) through a first breath intermediary 91B that comprises a condenser, an NS array and a DMS; and that passes this substanc(es) through a second breath intermediary 91C that comprises an NS array arranged to receive substances from a headspace sampler.

A blood pathway module 92A receives blood analytes and blood cell counts and passes this substance(es) through a first blood intermediary 92B that comprises a DMS and a biomarker analyzer.

A saliva module 93A receives blood analytes and saliva samples and passes this substance(es) through a first saliva intermediary 93B that comprises a DMS, an NS array and a biomarker analyzer; and that passes this substance(es) through a second saliva intermediary 93C that comprises a head space sampler and a NS array.

A urine and/or perspiration pathway module 94A receives urine and/or perspiration volatiles and passes this substance(es) through a first urine/perspiration intermediary 94B that comprises an NS array and a DMS; and that passes this substance(es) through a second urine/perspiration intermediary 94C that comprises a head space sampler and a NS array. The processed and/or interrogated substances are further processed and/or stored and the relevant results read out by one or more readout mechanisms 95.

Comparison of Medical Conditions.

The NS sensor array, illustrated in FIG. 2, and/or the DMS module, illustrated in FIG. 4, and/or a biomarker analyzer, illustrated in one embodiment in FIG. 5, may independently indicate that a first medical condition and/or a second medical condition, respectively, are present in the subject. It may be instructive to compare attributes of the first and second medical conditions, which may correspond to the same medical condition or may correspond to different medical conditions. Where the first and second medical conditions are the same, or substantially the same, confluence of the first and second medical conditions may confirm presence of this medical condition in the subject. Where one of the two embodiments shown in FIGS. 2, 4 and 5 indicates presence of a medical condition ("PMC") but the other embodiment does not indicate presence of any medical condition, the indicated presence of PMC may be accepted, subject to confirmation by more focused analyses.

In some situations, the embodiments described in FIGS. 2, 4 and 5 may indicate presence of a first and presence of a second medical condition, referred to as PMC 1 and PMC 2, respectively. Where at least one attribute in PMC 1 is inconsistent with at least one attribute in PMC 2, this may indicate that at most one of PMC 1 and PMC 2 is present, and subsequent analysis should focus on confirmation or refutation that each of PMC 1 and PMC 2 is present in the subject. Where each primary (or most relevant) attribute of PMC 1 is not inconsistent with each primary (or most relevant) attribute of PMC 2, this may indicate that a single medical condition, having at least one primary attribute from PMC 1 and at least one primary attribute from PMC 2, is present in the subject. Occurrence of this condition (first and second attributes, not inconsistent with each other) may help limit the search for presence of a single or primary medical condition in the subject.

Suitable Sources for Samples.

Blood, considered as a sample, has four major components: (1) erythrocytes (red blood cells, which lack a nucleus and transport hemoglobin and oxygen from the lungs to all living tissues in the body; produced from stem cells in the bone marrow; viable for about four months); (2) leukocytes, lymphocytes, granulocytes and macrophages (white blood cells; first responders for the immune system, as part of the human leukocyte antigen (HLA) system; seeks and destroys alien proteins on bacteria, viruses and fungi; produced from bone marrow stem cells and in the thymus gland; most are viable for 18-36 hours); (3) platelets (thrombocytes; fragments that lack a nucleus and provide clotting at a wound site; 13 different clotting factors are identified; which also fight infection by releasing proteins that destroy invading bacteria; effectiveness varies with the time of day; viable for 9-10 days); and (4) plasma (transports red cells, white cells, platelets, oxygen, nutrients, vitamins, electrolytes, metabolism waste products, hormones, enzymes, antibodies, other proteins, carbohydrates, and heat; produced from bone marrow stem cells). When blood of two persons is mixed together, with different markers or antigens on the red cell surfaces, these cells may agglutinate (clump together) or burst, both undesirable reactions. When agglutination (clotting) occurs, the blood mostly remains liquid (becomes non-liquid)

At present, 29 different human blood systems have been identified, with one or more antigens (a total of more than 100) for each of these blood groups. Approximately 30,000,000 possible HLA genotypes have been identified. HLA incompatibility between donor and donee is a continuing concern. Blood represents about 8 percent by weight of an adult human (4.5-6 liters). Blood components, especially the plasma, can be interrogated to identify the nutrients, electrolytes, waste products, proteins and antigens present, and their relative concentrations, to identify any medical conditions of concern. Reference ranges (minimum to maximum) for each of several substances can be established experimentally for a target person, and the corresponding present measurement can be compared with this reference range to identify any anomalies. This comparative approach can also be applied to compositions and concentrations of nutrients, electrolytes and waste products (exhaled breath, perspiration, saliva and urine). Blood components can be analyzed using a DMS module.

In the process of breathing, a human will inhale about 78 percent nitrogen, 21 percent oxygen, and 1 percent trace gases, such as Ar; and this person will normally exhale 78 percent nitrogen, 13.6-16 percent oxygen, 4-5.3 percent $CO_2$, 3-5 percent water vapor, and 1 percent trace gases (Ar, $H_2$, CO, ammonia, acetone, methanol, ethanol, etc.). The relative ranges of $O_2$ and $CO_2$, before and after a breath is taken, will vary the most, and the inhale/exhale changes in these two substances should be compared with reference ranges for change, for a reference person with each of several medical conditions. Percentages of exhaled substances, such as $H_2$, CO, ammonia, acetone, methanol and/or ethanol, should also be compared with corresponding reference ranges. Breath can be analyzed using an NS array or a DMS module.

A body decreases its core temperature by sweating, also referred to as evaporative cooling. The amount of perspiration lost by evaporative cooling is variable (100-8,000 mL/day), depending upon environmental conditions, age, gender, genetics, and the two most important factors, fitness level and body weight. Most of perspiration is water, but also includes a small amount of solute (0.2-1 percent). The solute may include Na (0.9 g/L), K (0.2 g/L), Ca (0.015 g/L), Mg (0.0013 mg/L), Zn (0.4 mg/L), Cu (0.3-0.8 mg/L), Cr (0.1 mg/L), Fe (1 mg/L), Ni (0.05 mg/L), Pb (0.05 mg/L), minerals, lactate and urea. Normal perspiration is mildly acidic, with pH lying in a range 4.5-7. Measured values of one or more of these chemicals, or of the pH, can be compared against a corresponding reference range after moderate to vigorous exercise, to estimate which medical condition(s) is/are present in a target person. Perspiration can be analyzed using a DMS module or an NS array.

Saliva is approximately 99 percent water and 1 percent electrolytes, mucus, glycoproteins, enzymes and anti-bacterial compounds. Saliva is super-saturated with selected ions, which act as a buffer to keep the pH of the mouth within a reasonable range, normally 6.2-7.4. A person of normal health will secrete 0.75-1.5 liters of saliva per day. This secretion decreases to approximately zero during sleep. Normal ranges for electrolytes found in saliva include Na (2-21 mmol/L), K (10-36 mmol/L), Ca (1.2-2.8 mmol/L), Mg (0.08-0.5 mmol/L), Cl (5-40 mmol/L), bicarbonate (25 mmol/L), and phosphate (1.4-39 mmol/L). Measurements for a target person can be compare with corresponding reference ranges to estimate which, if any, medical conditions are associated with this person. Saliva can be analyzed using an NS array or a DMS module.

Urine, when first excreted, is primarily water (95 percent), urea (($NH_2$)—CO—($NH_2$); 9.2 g/L), $Cl_2$ (1.87 g/L), Na (1.17 g/L), K (0.75 g/L), creatinine (0.67 g/L), blood urea nitrogen (BUN), and other dissolved ions and substances. Within two to four hours after excretion, urea partly decomposes into $NH_3$ and $CO_2$ molecules, often with an increase in pH. Measurements of one or more of these urine constituents for a target person can be compared with corresponding reference ranges to estimate which, if any, medical condition(s) is/are associated with this target person. Urea content should be promptly determined, no more than two to four hours after excretion, and the concentration differences compared with corresponding reference differences. As noted above, urea is often a constituent present in perspiration. Urine can be analyzed using an NS array or a DMS module.

The system disclosed here is an integrated package of several medical diagnosis approaches that can accept and separate gas and liquid components of body fluids, that can work cooperatively to identify presence of complex combinations of medical conditions, and that can analyze each component according to the most relevant and efficient methods available. First and second medical conditions, estimated to be present in the target person from results provided by the NS array, and/or by the DMS module, may differ from each other, or these estimated medical conditions may overlap. Each of these approaches has its own strengths, limitations, and scope of chemicals whose presence can be confirmed (or refuted). The individual diagnosis techniques are flexible and can be adapted to identify medical conditions that were not initially anticipated.

What is claimed is:

1. A method for analyzing body fluids comprising:
    collecting from a subject a set of body fluids,
    inserting the set of body fluids into a compact integrated analyzer comprising a plurality of analysis devices, the plurality of analysis devices comprising a nanostructure (NS) array, a differential mobility spectrometer (DMS), and a biomarker analyzer (BA) where the BA is a Centrifuge Assisted Bead Sedimentation Biomarker Analyzer (CASBA) or a Capillary Action Biomarker Analyzer (CABA), and
    displaying results of the analyses;
    wherein each NS array comprises an unfunctionalized NS and at least three functionalized NSs, each functionalized NS being functionalized to produce changes in discrete electrical parameter values (EPVs) to permit estimation of at least one concentration value of at least a first chemical,
    wherein each DMS is configured to distinguish between the relative amounts of a first ion associated with a second chemical and a second ion associated with a third chemical, the ions being formed by ionizing a portion of a fluid sample being processed through the DMS,
    wherein each BA is configured to determine a blood cell count and/or to estimate an amount of a biomarker in the fluid sample being processed through the BA,
    wherein the set of results comprises the relative amounts, counts, and/or concentrations determined by each analysis device, and/or calculated values or conditions derived from the relative amounts, counts, and/or concentrations determined.

2. The method of claim 1, wherein the conditions derived from the relative amounts, counts, and/or concentrations determined comprise one or more medical conditions associated with particular combinations or ranges of the relative amounts, counts, and/or concentrations determined.

3. The method of claim 1, further comprising separating a member of the set of body fluids into a first gas component and a first liquid component, processing the first gas component and the first liquid components separately, and volatilizing the first liquid component prior to processing.

4. The method of claim 3, wherein the separating comprises capturing airborne microdroplets.

5. The method of claim 3, wherein volatilizing the first liquid component forms a second gas component and a first residual component, and the method further comprises processing the residual component through the BA.

6. The method of claim 1, wherein the set of body fluids comprises a blood sample, and the method further comprises processing portions of the blood sample through the DMS and the BA.

7. The method of claim 1, wherein the set of body fluids comprises a breath sample, and the method further comprises processing portions of the breath sample through the NS array and the DMS.

8. The method of claim 1, wherein the set of body fluids comprises a saliva sample, and the method further comprises processing portions of the saliva sample through the NS array and the DMS.

9. The method of claim 8, wherein the method further comprises processing portions of the saliva sample through the BA.

10. The method of claim 1, wherein the set of body fluids comprises a perspiration sample, and the method further comprises processing portions of the perspiration sample through the NS array and the DMS.

11. The method of claim 1, wherein the set of body fluids comprises a urine sample, and the method further comprises processing portions of the urine sample through the NS array and the DMS.

12. The method of claim 1, wherein the set of body fluids comprises a blood sample, a breath sample, and a saliva sample.

13. The method of claim 1, wherein the set of body fluids comprises a blood sample, a breath sample, a saliva sample, and a perspiration or urine sample.

* * * * *